United States Patent [19]

Tepic et al.

[11] Patent Number: 5,851,985
[45] Date of Patent: Dec. 22, 1998

[54] TREATMENT OF TUMORS BY ARGININE DEPRIVATION

[76] Inventors: Slobodan Tepic; Pawel Pyk, both of Oberestrasse 20, CH-7270 Davos, Switzerland

[21] Appl. No.: 698,876

[22] Filed: Aug. 16, 1996

[51] Int. Cl.$^6$ .................................................. A61K 38/00
[52] U.S. Cl. .................................. 514/2; 514/21; 604/4; 604/5; 604/28; 210/195.2; 210/259; 210/500.23; 210/632
[58] Field of Search .................. 604/5, 28, 4; 210/195.2, 210/259, 500.23, 632; 514/2, 21

[56] References Cited

U.S. PATENT DOCUMENTS

| | | | |
|---|---|---|---|
| 4,955,857 | 9/1990 | Shettigar | 604/5 |
| 5,084,001 | 1/1992 | Van't Hooft et al. | 600/3 |
| 5,356,374 | 10/1994 | Hogan et al. | 604/4 |
| 5,403,917 | 4/1995 | Boos et al. | 530/351 |
| 5,409,813 | 4/1995 | Schwartz | 435/7.24 |
| 5,416,198 | 5/1995 | Anderson et al. | 536/111 |
| 5,419,759 | 5/1995 | Naficy | 604/5 |
| 5,514,379 | 5/1996 | Weissleder et al. | 424/426 |

OTHER PUBLICATIONS

Goldberg, Alfred L., et al., "New insights into proteasome function: from archaebacteria to drug development", *Chemistry & Biology*, vol. 2, No. 8, 1995, pp. 503–508.

Goldberg, Alfred L., "Functions of the Proteasome: The Lysis at the End of the Tunnel", *Science*, vol. 268, No. 28, 28 Apr. 1995, pp. 522–523.

Baracos, Vickie E., et al, "Activation of the ATP–ubiquitin–proteasome pathway in skeletal muscle of vcachectic rats bearing a hepatoma", *The American Phsyiological Society*, 1995, pp. E996–E1006.

Kettlehut, Isis C., et al., "Endocrine Regulation of Protein Breakdown in Skeletal Muscle", *Diabetes/Metabolism Reviews*, vol. 4, No. 8, 1988, pp. 751–772.

Medina, Ruth et al., "Increase in levels of polyubiquitin and proteasome mRNA in skeletal muscle during starvation and denervation atrophy", *Biochem. J.*, vol. 307, 1995, pp. 631–637.

Wing, Simon S., et al., "Increase in ubiquitin–protein conjugates concomitant with the increase in proteolysis in rat skeletal muscle during starvation and atrophy denervation", *Biochem. J.*, vol. 307, 1995, pp. 639–645.

Murray, Andrew, et al., The Cell Cycle—an introduction, Oxford University Press, 1993, pp. 40, 96–100, 105–106.

Reiken, Steven R., et al., "The Use of a Single Fiber Reactor for the Enzymatic Removal of Amino Acids from Solutions", *Biotechnology and Bioengineering*, vol. 35, 1990, pp. 260–267.

Rogers, Nature 220(5174): 1321–1322 (1968).

Lea et al., Cancer Biochemistry Biophysics 13(3): 171–179 (Jun. 1993) (Abstract).

*Primary Examiner*—Jean C. Witz
*Attorney, Agent, or Firm*—Karen Lee Orzechowski; Nath and Associates

[57] ABSTRACT

Method, compositions and apparatus for the treatment of tumors by systemic deprivation of an essential amino acid, preferably of arginine, by extracorporeal treatment of the patient's blood characterized by molecular exchange between the blood and a dialyzing fluid which contains most of the essential low-molecular substances found in blood plasma with the exception of at least one of the essential amino acids. The release of muscular protein amino acids can be limited by use of an insulin/glucose clamp. The treatment process can be used in conjunction with chemotherapy.

13 Claims, 4 Drawing Sheets

TREATMENT OF TUMORS BY ARGININE DEPRIVATION

FIELD OF THE INVENTION

The present invention generally relates to a method for the treatment of tumors, the apparatus for such a method of treatment, and the compositions used in such method of treatment. In particular, the present invention relates to a method for the treatment of tumors by depriving the tumor cells of an essential nutrient. More particularly, the present invention relates to a process for the treatment of tumors in a patient by dialyzing blood from the patient to remove at least one essential nutrient for a time sufficient to cause tumor cells to die.

BACKGROUND ART OF THE INVENTION

Cancer is the second (after cardio-vascular diseases) leading cause of death in the developed world. An enormous research effort of the last decades has produced dramatic advances in understanding mechanisms of transformation, i.e., of the process by which a normal cell becomes cancerous. The pace of discovery has quickened in the last several years with new tools of molecular biology coming to aid, many of which have actually been developed in the effort to understand cancer. Unfortunately, the treatment of cancers has not seen much improvement, and with several notable exceptions, the five-year survival rate has remained about the same throughout this period of several decades—some 50% overall.

In multicellular organisms, division of an individual cell is an event controlled by the needs of the whole organism. While most cells are capable of dividing, or mitosis, they rarely do so if not stimulated to by the conditions of the tissues they form. If an injury is inflicted, for example, the local, as well as the infiltrating cells, may respond by mitosis and tissue regeneration in order to repair the damage. Once the repair is done, the cells return to their quiet existence without proliferation. In some cases, the division of cells is a rule rather than exception. For example, in the bone marrow, cell proliferation continuously provides for blood cells replenishment. The intestinal lining cells also proliferate continuously in order to make up for the loss of the outermost layers caused by in the harsh environment where cells do not last very long. In a healthy individual the steady state is well controlled by local conditions of blood supply, geometrical intercellular relationships, territorial integrity, as well as by systemic factors such as growth factors production, nutrient availability, and the like. The imbalance between cell proliferation and cell death caused by the loss of normal mitotic cycle controls leads to a tumor or neoplasm. If the growth remains local, the tumor is said to be benign, and a complete surgical resection leads to cure. Some tumors, however, possess mechanisms allowing the tumor cells to spread into and proliferate in other tissues. Such tumors are characterized as malignant, and are referred to as cancers. The spread of the tumor cells into other tissues involves the steps of cell separation from the local tumor mass, entry into the blood or lymphatic circulation, transport to another site, entry into that site and continued growth. Treatment of cancers which have spread to various locations, and have formed the secondary tumors, or metastases, is very difficult. In order to succeed, the attack must be selective. Finding selective strategies is the main topic of clinical cancer research efforts. Indeed, the possibility of discovering a successful cancer treatment must be the main motivation of all research on cancer and related aspects of cell biology.

In general, tumors appear to be monoclinal, i.e., all of the tumor cells have descended from a single progenitor cell. Transformation which has made the progenitor cell cancerous is a slow, multiple stage process requiring, in most known cases, a number of specific genetic defects. The genes affected are called oncogenes and the products they encode are called oncoproteins. The changes in DNA sequence may be produced by chemical carcinogens, ionizing radiation, or viral infection, but many other factors play a role in the process. The end effect by which the cell is recognized as tumorous is the apparent lack of proliferation control. To decide whether a cell is transformed, or not, one can make two functional tests: (1) if the cell divides in suspension, i.e., without "anchorage"; or (2) if the cell grows into a tumor in a nude mouse (a mouse with no immune system), the cell most likely is transformed. The discovery of the first oncogene inspired a great deal of optimism based on the hope that perhaps only that single defect needed to be somehow corrected to cure cancer. But tens of oncogens (just over one hundred by now) were identified very quickly and it became clear that cancer was what it has been taken for—a multitude of diseases. Nevertheless, the multitude of diseases that make up cancer all do lead to very similar manifestations. The ultimate common path in the death of the patient keeps the hope alive that there might be a single cure yet.

As of now, the surgical treatment, whenever possible is still the most efficient treatment. If the cancer has not spread from its primary site, the complete resection of the tumor leads to cure of the cancer. If surgery is not possible, or the spread of cancer cells has occurred prior to surgery, chemotherapy may kill some types of cancers. Not all types of cancer are susceptible to chemotherapy, however, and the treatment is, in any case, a balancing game—killing as much of the cancer without killing the patient. The toxic chemicals used for chemotherapy are specific to different phases of the cell cycle, and only a number of cells will be killed by any single dose—some of them cancerous, some of them, normal cells that proliferate continuously (most importantly cells in the bone marrow and intestines). Treatment protocols have been developed over years of experimentation and clinical use aimed at combining different drugs in ways to maximize the chances of cancer elimination. Radiation treatment is another possibility, used mostly in conjunction with surgery. In this case, again, the problem is differentiation sufficiently between the normal and cancerous tissue. Even when the cancer is spatially distinct, the methods of radiation delivery available today are not very precise. Asynchronous cell proliferation is a major drawback here as well because cells are not equally susceptible to radiation in different parts of the cycle.

Other physical treatment approaches have been tried and have to a great extent remained experimental—local hyperthermia (produced by ultrasound), for example, had been employed as an adjunct to chemotherapy.

Most promising of the new approaches are those based on using either naturally occurring, or engineered, substances that can interfere with cancer growth and spread: Tumor Necrosis Factor has been identified and tested in native and modified forms; Lymphokine Activated Killer cells have been prepared and used in conjunction with interleukine-2; vaccination against melanoma, which appears to have very characteristic surface markers, is under development; and "magic bullet" drugs; i.e., cytotoxic drugs targeted by the aid of specific antibodies, show a great promise against cancers that display antigens not found on the normal cells. As the details of transformation fill in, new possibilities will certainly open up. Just over one hundred oncogens have been identified. The proteins they encode are found at different locations within the cell, and a troubling possibility exists that many cancer cells may not be identified as such by their surface antigens. Entering the cell in order to intervene, while not impossible, is going to be a lot more difficult than to exert the action on the surface and nothing very efficient has been done even for those types of cancer that do possess strong surface antigens.

Of the existing, clinically accepted and widely practiced anti-cancer treatments, the most relevant to this invention is asparaginase treatment which is used primarily in the combined chemotherapy treatments of the childhood acute leukemia. Anti leukemic effects of asparaginase were discovered by chance in the fifties, understood in the sixties and brought to clinical use in the seventies. The treatment is based on a peculiar property of leukemic cells—they do not produce asparagine, a non essential amino acid. Unfortunately, when exposed to repeated challenges, these cells adapted and turn on the production of asparagine, thus becoming resistant to any further treatment. The other problem is the antigenicity of the enzyme—injected i.v. or i.m. The enzyme causes immune responses which, in addition to rather serious other side effects, may lead to a fast neutralization of circulating enzyme. In spite of these restrictions, asparaginase is today routinely used in combined protocols for childhood acute lymphocytic leukemia.

The unique approach presented here is based on the most universal of the features of all tumor cells—the property that in fact defines them as tumorous—their propensity to grow and proliferate under conditions where normal cells would not. The basic strategy calls for manipulating systematically those proliferations conditions that can affect the cell cycle, within the physiologically admissible bounds, in such a way as to allow tumor cells to cross those critical cycle check points and expose themselves to the hazards of insufficient essential nutrient supply. The preferred targets are essential amino acids, particularly arginine. Tumor cells demonstrate increased requirements for arginine, as we have shown by in vitro work. This requirement is for non-protein use, most likely for production of polyamines via ornithine, and possibly of the nitric oxide. Deprivation of arginine is thus more efficient in killing tumor cells than deprivation of any other essential amino acid. Tryptophan is also of special interest since its presence in the fibrillar proteins of the muscle tissue is very small and therefore the attempt of the body to maintain the normal systemic level is easier to overpower by the extracorporeal blood treatment.

SUMMARY OF THE INVENTION

The present invention relates to a treatment of tumors based on an extracorporeal blood treatment characterized by molecular exchange between the blood and a dialyzing fluid across a molecular sieve membrane, whereby the conventional dialyzing fluid is supplemented by a plurality of low molecular weight organic and inorganic substances at concentrations essentially equal to those found in the normal blood plasma with the exception of at least one essential nutrient, preferably an essential amino acid, which is either not present, or is present at a substantially lower concentration. Additionally, the dialyzing fluid may contain molecular factors, at normal or at elevated concentrations, involved in the cellular processes of protein synthesis and degradation in order to limit the release of amino acids from non-essential cellular proteins, mainly fibrillar muscle proteins. These factors are branched side chain amino acids (leucine, isoleucine and valine, glutamate, insulin, insulin like growth factors and growth hormones.) Insulin was found to be the most effective. Delivery of insulin must be balanced by an appropriate rate of delivery of glucose in order to avoid hypoglycemia. Chemical inhibitors of the protein degradation pathways may also be added to the dialyzing fluid, as well as antibiotics needed to reduce the risk of infection.

At the same time concentrations of the promoters of protein degradation are lowered by dialysis, particularly concentrations of glucocorticoid, glucagon, thyroid hormones, Tumor Necrosis Factor and interleukine-1.

Temperatures of the dialyzing fluid are also controlled, preferentially to subnormal levels in order to reduce the muscle protein breakdown in response to removal of the targeted essential amino acid. A controlled level of hypovolemia also limits the release of amino acids from the muscle tissue, by affecting the blood perfusion of the peripheral organs.

Equilibrating mass transport between the blood and the appropriate dialyzing fluid results in a sufficiently powerful systemic-level control with sustainable extracorporeal blood flow rates, so that a continuous treatment of several days can be carried out leading to selective killing of the tumor cells. This result can be accomplished due to the relaxed cell cycle control mechanisms found in all tumor cells. Upon deprivation of an essential amino acid, healthy, normally cycling cells enter the cycle and are kept in the rest phase where they can easily survive the harsh conditions of deprivation. In contrast, tumor cells are less restricted and will proceed into the cycle finding themselves vulnerable to conditions of deprivation. During the first cycle of deprivation, a majority of cycling tumor cells proceed over the restriction point into the S-phase (DNA synthesis) and are readily killed after, for example, no more than 72 hours of arginine deprivation. The few survivors among the cycling tumor cells can again be sent across the restriction point by re-supplying the deprived essential amino acid during a time which is too short for the normal cells to enter the cycle, and then eliminated by repeated deprivation. Programming of such cycles is preferably achieved by switching between the appropriate concentration formulations of the dialyzing fluid.

This method of treatment can be readily combined with a suitable protocol of chemotherapy. Deprivation of arginine causes most tumor cells to crowd into and to get arrested in the S-phase, while most normal cells manage to complete their cycle and exit into the rest phase ($G_0$). S-phase-specific drugs can thus be used in significantly escalated doses. The preferred mode of drug delivery is by loading the drug into (or mixing it with) the dialyzing fluid, thus avoiding any risk of overdose, but also readily removing the drug from circulation by switching to a drug-free dialysate at the end of the drug treatment, before the healthy cells are allowed back into the cycle. Alternatively, drugs can be infused directly into the blood, taking into account kinetics of removal by the continuous dialysis. As soon as the infusion is stopped, dialysis will quickly reduce the concentration of the remaining drugs.

We have now discovered by performing in vitro work on seven different human cancer lines that arginine is the best target for amino acid deprivation because arginine is used in disproportionate amounts by all cancer cells tested for production of proteins, but also of polyamines. The "killing window" is defined by concentrations below 10 micro molar and by deprivation time longer than 72 hours. Normal cells exit the cycle and reemerge from the rest phase apparently undamaged after even ten days of arginine deprivation.

We have also discovered by performing in vivo experiments on healthy large dogs that the cancer killing concentrations of arginine are attainable and sustainable for up to three and a half days without major systemic complications. This resultant time period was achieved by the application of the continuous dialysis described above and by controlled infusion of both insulin and glucose.

Arginine has a special role in the physiology of mammals. The main pathway for elimination of excess nitrogen is the urea cycle, whereby liver cells use a set of enzymes which turn arginine into ornithine, ornithine into citrulline, and citrulline back into arginine with the net effect of releasing nitrogen from ammonia (which is produced by ultimate degradation of amino acids) as a constituent of urea. Should this process be inhibited by the lack of arginine, the predictable outcome is accumulation of highly toxic ammonia. This phenomenon seems to have escaped the attention of many investigators who have worked on arginine degrading enzymes. Our preferred embodiment avoids this potential toxicity by the concurrent removal of ammonia by hemodialysis. A further advantage of the dialysis of the present invention is the possibility of removal of citrulline and ornithine which are precursors of arginine (these metabolic processes are not confined to liver).

Deployment of arginine decomposing enzymes is possible as well, but it must be accompanied by dialysis in order to remove ammonia. The risks of ammonia accumulation, and hence the need for removal of ammonia, may be partially or completely offset by the deployment of protein breakdown inhibitors. In order to minimize immunological side effects caused by i.v. or i.m. injections of enzymes, a new method is disclosed whereby the enzyme is inhaled as an aerosol. All known arginine decomposing enzymes are large proteins which cannot enter blood circulation through the respiratory membrane. Instead, the amino acids, specifically arginine, will diffuse out from the blood capillaries of the lungs and decompose within the fluid layer which coats the lungs, and which contains the enzyme. This mode of operation has the potential for a much higher efficiency than hemodialysis since the artificial membrane of dialyzing filters is typically 1.8 square meters and the extracorporeal blood flow through the lungs is equal to the total heart output of about 5 liters/minute. For a further reduction of the risks of immune response the enzyme can be encapsulated into a suitable polymer or conjugated with PEG. As the enzyme degrades and loses its activity, it is eliminated from the lungs by a natural process of mucosal excretion.

Alternatively, dialysis can be performed using conventional dialyzing solutions, while some, or all, of these substances, as well as any necessary adjuvants (e.g. glucose with insulin), can be delivered by a controlled infusion into the return line of the extracorporeal circuit. This embodiment constitutes a simple controller of the systemic concentration of these substances. The performance of the controller is dependent on the blood flow and the efficiency of the filter, which is predictable, can be monitored essentially on line, and the necessary adjustments of the infusion rate are easily implemented.

DETAILED DESCRIPTION OF THE INVENTION

Proteins, protein synthesis and turnover, and the cell cycle

Proteins are major macromolecular constituents of living cells involved in all crucial cellular functions including cell growth and division. The building blocks of all cellular proteins are 20 amino acids (lysine, arginine and histidine with basic side chains; aspartic and glutamic acid (or glutamate) with acidic side chains; asparagine, glutamine, serine, threonine, valine, leucine isoleucine, proline, phenylalanine, methionine, tryptophan and cysteine with non polar side chains). Tens of those (arginine, threonine, methionine, lysine, valine, leucine, isoleucine, histidine, phenylalanine and tryptophan) are essential for vertebrates, i.e. they cannot be synthesized from any other substances and thus must be taken through diet (arginine can be synthesized, but not in sufficient amounts).

Intracellular proteins undergo a constant turnover process. Turnover rates of proteins vary greatly and depend on their intrinsic properties and functions. On average, in an adult human about 400 grams of proteins are produced and degraded every day. About 300 grams are produced from recycled amino acids; the balance of 100 grams are produced from fresh amino acids supplied by dietary protein. Dietary proteins are hydrolyzed into amino acids or oligopeptides and absorbed in the gastrointestinal tract.

Synthesis of proteins is catalyzed on the ribosomes which read the sequence of amino acids to be polymerized from the molecules of mRNA. Intracellular transport and coding of the amino acids is accomplished by tRNA. The rates of protein synthesis are controlled by initiation factors, which will respect the availability of all essential nutrients, amino acids in particular, and respond to external signals e.g. growth factors.

Two major pathways for intracellular protein breakdown are lysosomal and proteasomal (ubiquitin, ATP-dependent). The proteasome pathway is more selective and will degrade almost exclusively those proteins which are specifically tagged for hydrolysis by ubiquitin conjugation. This is the case with damaged or mutated proteins, but also with regulatory proteins such as cyclins (Goldberg, A. L.: Functions of the Proteasome: the Lysis at the End of the Tunnel. *Science* 268, 522–523, 1995). Both mechanisms are responsive to extracellular signals, and insulin is one of the most potent inhibiting hormones (Kettelhut, I. C., Wing, S. S., Goldberg, A. L.: Endocrine Regulation of Protein Breakdown in Skeletal Muscle. *Diabetes/Metabolism Reviews*, Vol. 4, No. 8, 751–772, 1988). At the same time insulin stimulates protein synthesis, especially in muscle, and transports mechanisms of amino acids and glucose into the tissue. These effects, coupled with the stimulation of insulin release following food intake, are geared toward an efficient process of amino acid incorporation into proteins.

Other substances which have been shown to inhibit proteolysis, mostly by in vitro experiments on cells and tissues, are branched side chain amino acids leucine, isoleucine and valine, but also glutamate, insulin-like growth factors (IGF-I and IGF-II) and growth hormones. Several peptide aldehyde inhibitors of the proteasome have also been identified, e.g. MG 132 (Cbz-Leu-Leu-Leucinal) (Rock, K. L. et al., & Goldberg, A. L.: Inhibitors of the proteasome block the degradation of most cell proteins and the generation of peptides presented on MHC-class I molecules. *Cell* 78, 761–771, 1994), as well as the natural product, antibiotic lactacystin (Feanteany, G., Standaert, R. F., Lane, W. S., Choi, S., Corey, E. J., Schreiber, S. L.: Inhibition of proteasome activities and subunit-specific amino-terminal threonine modification by lactacystin. *Science* 268, 726–731, 1995).

Protein degradation has been shown to be stimulated by glucocorticoids, glucagon, thyroid hormones, Tumor Necrosis Factor and interleukine-1. In order to limit the capacity of muscle protein breakdown to compensate for depletion of say arginine, these factors should be removed from circulation to the extent possible.

Cell growth and division are thus subject to coordinated processes of protein synthesis and breakdown. Since the protein turnover is not 100% efficient, a fresh supply of amino acids is crucial for the cell survival, growth and division. Healthy cells will exit the cycle in response to unfavorable external conditions—in fact, in an adult organism, a great majority of cells are in the rest phase. Rest phase requirements for amino acids are reduced since there is no net growth. There is also a factor two reduction of protein turnover in $G_0$ compared to $G_1$.

Tumor cells, by definition, have lost some of the control mechanisms of growth and division. While tumor cells can be arrested in growth as well, it is still unclear if they are able to enter a true $G_0$. The basis of this invention was the assumption, which we have now proved on a number of cancer lines in vitro, that by controlling the external conditions of an essential nutrient supply, a transformation-selective effect can be exerted on a mixed population of cancerous and healthy cells, leading to a faster demise of cancer cells.

While any of the amino acids could be selected as a control parameter—lack of any single one totally inhibits protein synthesis—taking a nonessential one may require tighter control to fight cells ability to compensate by increased synthesis. This strongly suggests controlling the concentration of one of the essential amino acids. Amino acids cross the cell membrane by mostly active transports, but the internal pool, with some exceptions, is most of the time near equilibrium with the extracellular fluid, which in turn is near equilibrium with blood levels. Thus controlling the level of at least one, and preferably only one, essential amino acid in the blood circulation should give an effective control input to the cell protein synthesis process.

Strategy

Our in vitro work (D. N. Wheatly: Personal communication) with HeLa Cells (human cervical carcinoma) and early passages of human fibroblasts has established limits of survival and recovery after different items of arginine deprivation. Precise cloning studies (counting cell colonies which can be revived by re-supply of the normal medium) showed that no recovery of HeLa cells was possible after 72 hours of arginine deprivation (the small number of survivors at 72 hours of deprivation would die during the next three days in the normal medium). By 96 hours of deprivation all HeLa cells were dead. In contrast, healthy fibroblasts could be recovered after even 10 days of deprivation.

Further work established that arginine concentration of 1 micro mole per liter had essentially the same effects as total deprivation. At 40 mircomolar, HeLa cycle was already disturbed, and killing of the cells started below 10 mircomolar. Thus our target "killing zone" for HeLa cells is 1 to 10 micromolar concentration of arginine during three to four days of deprivation.

Very similar responses were seen with six additional human cancer lines (osteosarcoma, lung carcinoma, brain astrocytoma, prostate, breast and colon adenocarcinomas). Deprivation of other essential amino acids showed much slower killing of tumor cells and a smaller difference to healthy cells. Capitalizing on those differences is still possible, but it requires more complex approaches and deployment of control strategies based on the concept of controllability. We have thus placed a strong priority on working with arginine.

Our current strategy, based on the data from the in vitro studies and the feasibility, in vivo, experiments on healthy dogs, calls for a single session of cancer treatment consisting of the first periods of deprivation of three to four days, followed by about 12 hours of normalized arginine supply, followed by another three to four days of deprivation. This attack should kill most of the cancer cells in the immediate proximity of blood vessels, but there are good indications that even the deeper layers of non dividing cancer cells would be killed.

In the case of relapse, repeating these sessions should not pose great difficulties since only minimal side effects are expected, and it is highly unlikely that resistance to this treatment could develop.

Implementation

In this section a detailed description is given of the preferred implementation schemes of the strategy presented above. Two basic approaches to the treatment are possible:

(1) to exert control over the concentration of the selected amino acid in an extracorporeal circulation apparatus resembling that used for dialysis;

(2) to exert the control intracorporeally, by decomposing the selected amino acid by enzymatic means. Increasing the concentration in both cases is done by injecting the required amount of the amino acid (at the required rate).

The first method can be readily implemented, using only approved substances (drugs) and procedures. It has been tested and shown to have sufficient capacity. The second method is more convenient to implement, and most efforts in this field of medical research have been directed towards discovery, characterization and preparation of suitable enzymes. In the specific case of arginine, as discussed earlier, enzymatic intracorporeal degradation is likely to result in accumulation of highly toxic ammonia (due to blockage of the urea cycle), and our approach calls for the use of dialysis for the removal of ammonia. The risks of ammonia accumulation, and hence the need for removal of ammonia, may be partially, or completely, offset by the deployment of protein breakdown inhibitors. Delivery of the enzyme into the lungs, proposed hereby, provides a large surface for exchange of arginine, but in contrast to all known approaches to respiratory drug delivery (whereby the drug is to be absorbed through the respiratory membrane), the enzyme (the "drug") in fact remains extracorporeal. We shall still, in order to distinguish between the two methods, refer to this approach as intracorporeal.

Figure 1:
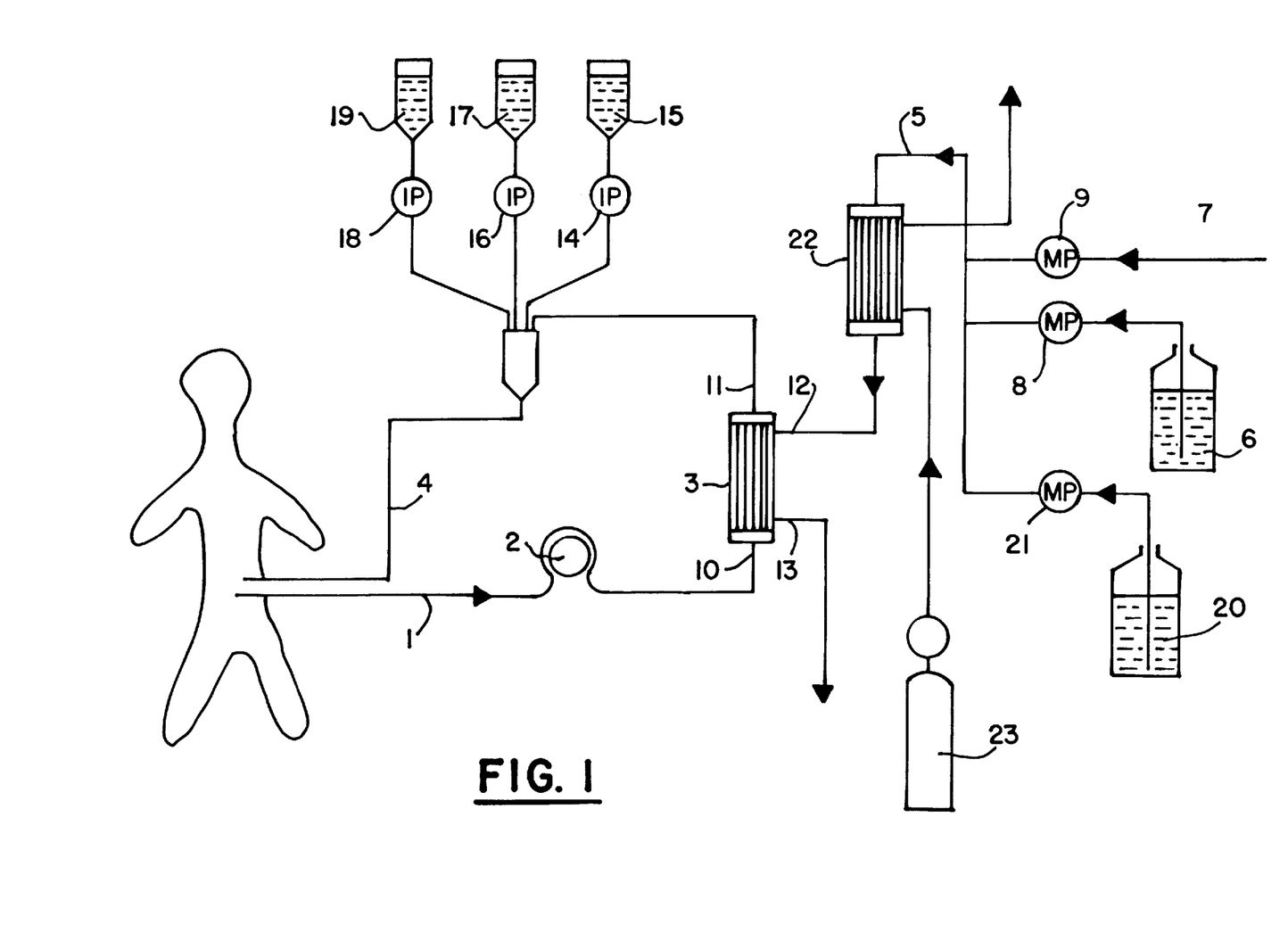
FIG. 1 depicts a schematic diagram of an apparatus of one embodiment of the present invention.

An extracorporeal control approach requires connections to blood circulation, preferably by central access catheters which are commonly used for larger flows needed for heart/lung machines. FIG. 1 shows an apparatus of one embodiment of the present invention in a simple configuration whereby the blood is taken out of the body through a blood line 1, pumped by the pump 2 through a filter 3 and back into circulation through a blood line 4. Dialyzing fluid 5 is pumped in the counterflow direction through the filter 3. Dialyzing fluids are prepared for the concentrate 6, which is diluted with water 7 (usually in the ratio 1:34) by metering pumps 8 and 9.

The filter 3 is preferably a hollow fiber type (alternatively flat membrane type) with the blood moving through the fibers. The extrafibrilar space between the hollow fibers is flushed by the dialysate. The flow through the extrafibrilar space is directed in the opposite direction from that of the blood. The wall of the fiber is a molecular sieve allowing passage of only low molecular substances and water. The cut-off of the sieve is a few thousand Daltons, preferably 5 to 50 thousand. Conventional, polysulfone, "regular flux", filters have a cut-off of 8000 Daltons; "high flux" filters are typically about 35000 Daltons. Amino acids pass through the fresh filter with little impediment. With time, as the filter gets coated by a gel layer of plasma proteins, its efficiency drops but typically to some equilibrium value determined by the ultimate thickness of the gel layer. Mass transport across the membrane will tend to equilibrate concentrations, so that concentration of any molecular species in the blood at the outlet 11 will approach the concentration of that same species in the dialysate at the inlet 12. At the same time concentrations in the dialysate at the outlet 13 will approach those of the blood at the inlet 10. By molecular exchange it is thus possible to control the level of any substances in the blood which is free to cross the filter. Specifically, in order to remove one and only one amino acid from the blood, a dialysate (concentrated factor 35 for convenience of supply) can be prepared which contains all other amino acids in desired concentrations, with the selected one omitted from the mixture.

Other substances needed for the therapy may be injected into the blood after the filter, e.g. insulin 15 by the pump 14, glucose 17 by the pump 16, and a solution of sodium phosphate 19 by the pump 18. Phosphate cannot be admixed to the concentrate 6 which contains calcium since the solubility of calcium phosphate is very low.

Conventional dialysis machines have a possibility of using either acetate or bicarbonate based dialysis. Bicarbonate dialyzing fluid is prepared by diluting two concentrated solutions. In the animal experiments we have opted for the use of acetate dialysis for practical considerations. If bicarbonate dialysis is used, the machine has to be cleaned every several hours, which would mean having two machines in order to switch without interruption. Otherwise, bicarbonate dialysis causes in general less side affects and would have been preferred. For the human patients, bicarbonate dialysis should be the method of choice.

The possibility of mixing from two concentrates with the existing hardware systems opens up the possibility of using a conventional concentrate (acetate based) on one side and delivering the supplements from the container 20 on the other side by the metering pump 21, FIG. 1.

In the animal experiments we have used a conventional, acetate based concentration (with major inorganic salts) supplemented by a "cocktail" of amino acids, water-soluble vitamins and antibiotics. Content and preparation procedures are described later.

Figure 2:
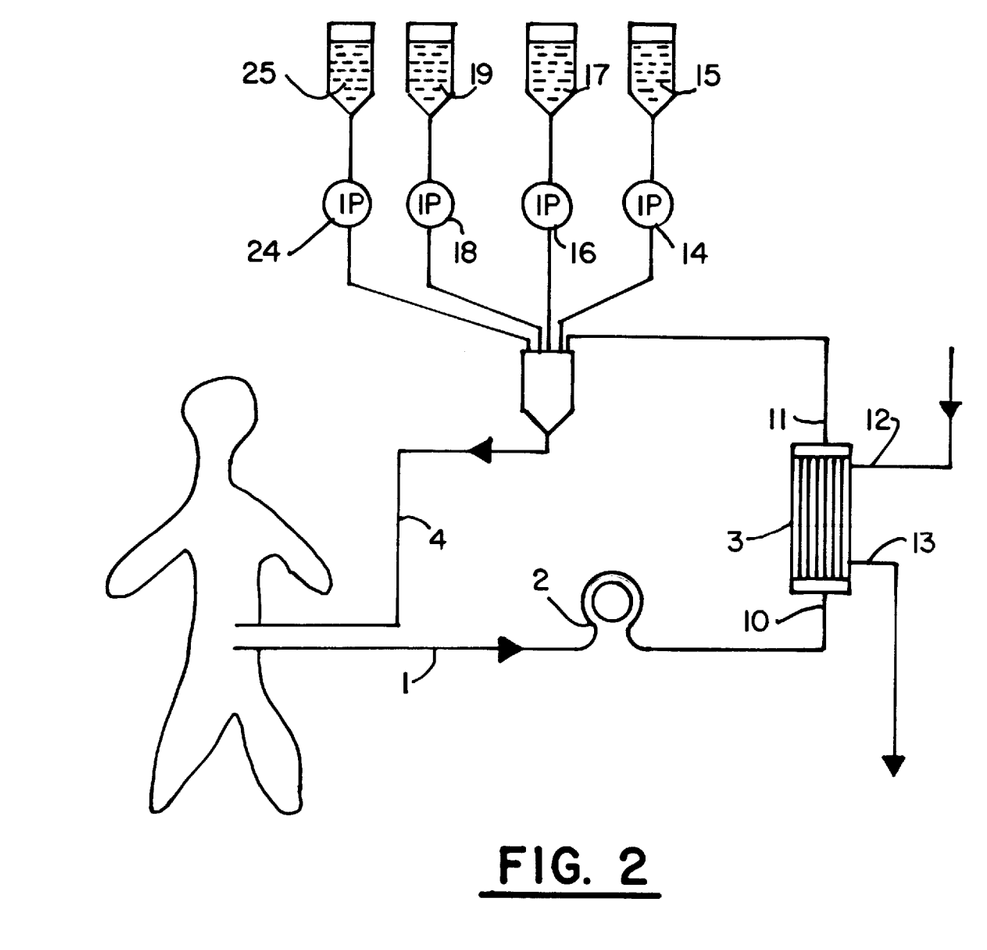
FIG. 2 shows a schematic diagram of another embodiment of the present invention in which all of the amino acids are removed by dialysis and the selected replacements are injected into the blood stream.

Alternatively, all amino acids could be removed at first, and those that are to be maintained, can be injected into the blood stream after the filter, as shown FIG. 2. The first option is preferable for its simplicity of control and safety in use because there is no risk of overdose. The second option may be preferable in practical terms of preparation, shelf life, and distribution of therapeutic substances to the users. There is not much difference in terms of wasting these substances. In both cases, the dialysate leaves the filter and is discarded with essentially blood level concentrations of all crucial constituents. While the cost of substances discarded with the dialysate may be too high for dialysis of chronic renal failure patients, it should be of little concern for this acute treatment of cancer patients.

The methods and apparatus of the present invention can also be utilized for the treatment of renal failure patients as well. Loss of amino acids is a major concern in the treatment of chronic renal failure patients. As discussed earlier, lowering the systemic concentration of any amino acid triggers the process of muscle protein breakdown. Once initiated, this process will run its course during several hours. By now, the patient is taken off the machine and there will be an overshoot of circulating amino acids, which can be only partially re utilized for protein synthesis. The rest are metabolized, producing a new burden of waste products which these patients already have difficulty eliminating in the first place. Supplementing amino acids after a session of dialysis has been tried clinically, but as expected from the logic of these events, it has not helped. After the session there is an excess of amino acids produced by the protein breakdown. In some patients these events lead to an uncontrollable, terminal protein loss (these patients are referred to as "shrinking patients"). Supplementing the dialysate with the appropriate mixture of amino acids should alleviate this problem. The precise composition of the mixture is not of great importance here, and for this purpose, amino acids can be produced by a simple, economically viable, process of protein hydrolysis, for example of casein (instead of re-mixing separated, purified, amino acids as is done with conventional amino acid infusion mixtures).

Another advantage of using a dialyzing fluid which is essentially a growth medium (as presented by the arrangement on FIG. 1) is of indirect, but important impact that extracorporeal blood treatment has on the proposed protocols. It has been recognized for many years that circulating blood through an extracorporeal circuit leads to a loss of blood cells, mostly of thrombocytes. Thrombocytes are activated leading to their aggregation and removal from circulation in blood clots which form both within the extracorporeal circuit and within the body. While this loss is of clear concern in chronic renal failure patients, it is tolerated since thrombocytes recover very rapidly and reach normal levels before the next session of dialysis (which is given typically three times per week). For our treatment, which calls for uninterrupted sessions of several days duration, loss of thrombocytes has proved a limiting factor. The conditions can be improved by deploying anti-aggregation measures (for example, giving the patients prostacyclin or its stable analogs), or in the case of a critical loss by a transfusion.

The process of thrombocyte aggregation is most likely initiated by the cells which cover the filtration membrane from the blood side. We have carefully observed the initiation of thrombi formation—it always starts at the outlet of the blood and the inlet of the dialysate. In three serially connnected filters we have employed several times, it was the last filter in the path of the blood (and the first in the path of the dialysate) which was always the first to show clot formation. The problem seems very clearly to be caused by a metabolic stress that the cells adhering to the membrane would be exposed to. If the dialysate is running in a closed loop, thus eventually reaching the composition of plasma (with low molecular weight constituents), there is only a minimal loss of thrombocytes up to eight days of interrupted extracorporeal circulation.

In our experiments on dogs we have used a dialysate which is essentially of the same composition as the cell growth media (minus arginine, citrulline, and ornithine which the normal cells do very well without). As we continued to lose the thrombocytes even with this composition of the dialysate, we finally realized that the missing substance was oxygen. To prevent formation of gas bubbles which may accumulate on the dialysis side of the filter fibers, thus reducing its effective area, the dialysate is degassed before entering the filter. This induced a state of hypoxia in the cell (which coat the membrane and are thus dependent on mostly diffusion for transport of all metabolites) near the dialysate entry. These cells respond by producing factors leading to thrombocyte aggregation (by analogy to much studied phenomena in tissues).

The problem is readily resolved by saturating the dialysate with oxygen, as shown in FIG. 1. To avoid any risk of blood out-gassing once it is returned to the patient (since the pressure in the filter is several hundred millibars higher than in the body), a mixture of 20% oxygen and 80% helium can be used to saturate the dialysate. This may be accomplished by bubbling the gas through a dialysate, or preferably, by passing the dialysate through a fiber oxygenator, 22, whereby the dialysate, 23, is pumped though the fibers and the gas mixture, 24, through the jacket. This effectively converts the dialyzing filter into a bioreactor for the patient's cells which coat the membrane.

Typical blood flows on normal dialysis machines range from 150 to 500 ml/min. Since the filter is of finite size the concentration of the substance which is being removed can only approach zero on a single pass through the filter. For a given size of the filter there is always an optimum flow rate of the blood that will result in the maximum absolute removal of the unwanted substance. We have used in our in vitro experiments with fresh blood, and in in vivo experiments on dogs, polysulfone filters of 1.8 $m^2$, with either 8000 Daltons cutoff or 35000 Daltons cutoff, which had the best performance at 300 to 400 ml/min blood flow, with the dialysate flow at 500 ml/min. Single pass removal was typically between 60 and 80% with the higher values for the fresh filter.

Pumps and filters must be designed to minimize damage of the blood cells. The technology used for dialysis and blood oxygenating machines can be readily applied.

The arrangement shown on FIG. 2 has all the essential elements shown on FIG. 1. The difference is in the constituents of the dialysate and the need for at least one additional infusion pump to deliver a concentrated solution of amino acids, water soluble vitamins and antibiotics. These substances could, of course, be prepared and delivered as separate solutions using several infusion pumps.

Figure 3:
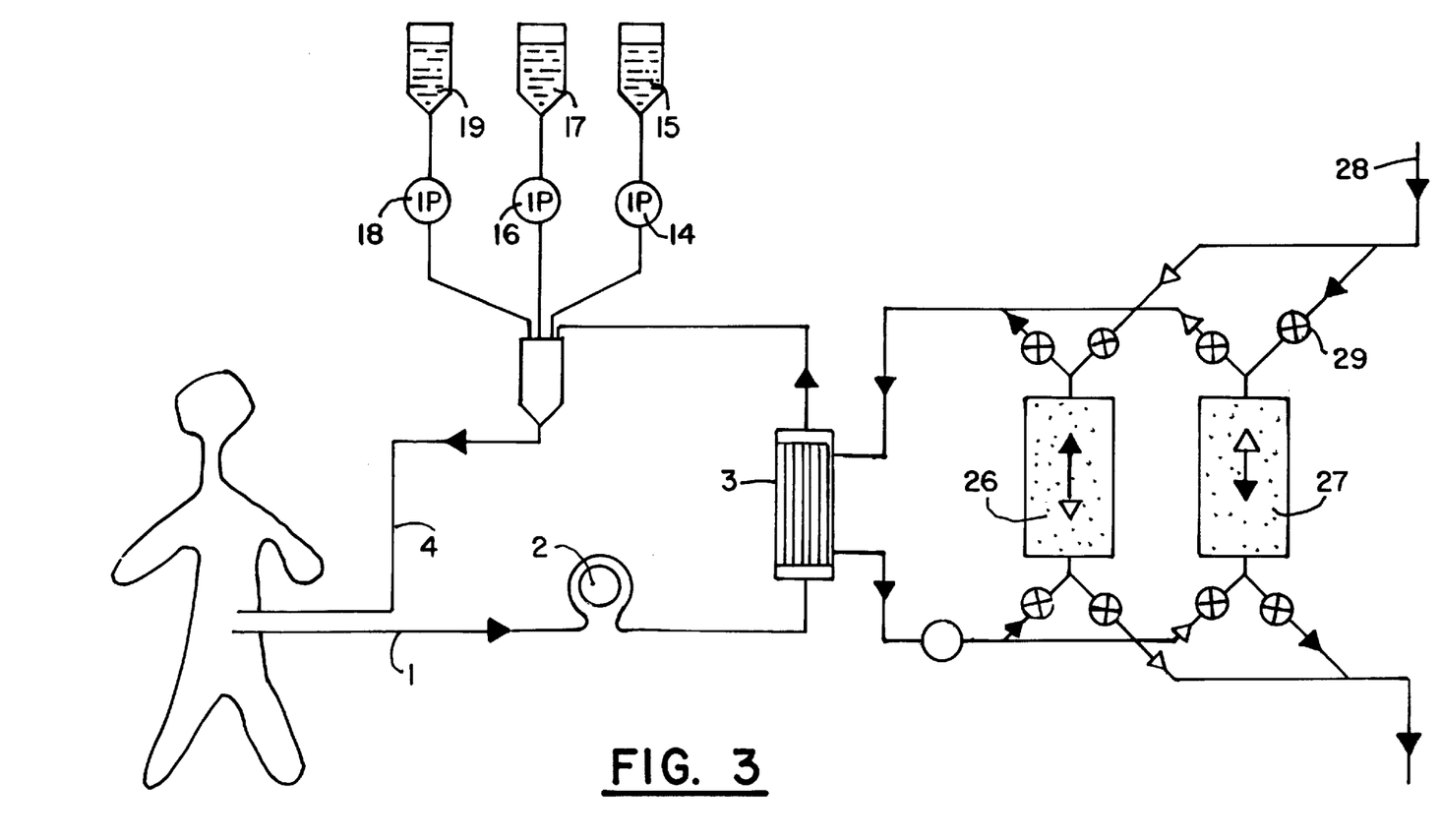
FIG. 3 shows a schematic diagram of another embodiment in which batch processing of the dialyzing fluid is conducted.

FIG. 3 shows another arrangement whereby only a batch amount of dialysate is used in order to reduce the demand on the body to replace many other low molecular substances present in the blood plasma, which are either not known or cannot be easily produced, and are therefore dialyzed out from the patient. This batch amount of dialysate may then be processed for removal of the targeted amino acids, either on-line, or off-line (for this, two batches can be alternated). One-option for on line operation is to use an affinity filter to remove arginine and lysine which have basic side chains and could be easily discriminated form the other amino acids. A fairly large amount of the affinity media is needed—about 50 kg for one day of operation. Regeneration of the column is possible, of course; a practical solution would probably call for two columns of 10 to 20 kg each, which are being alternated between on line operation and regeneration. This arrangement is shown on FIG. 3, with two affinity columns 25 and 26. Off-line operation calls for the same column arrangement, but a batch of dialysate is collected first and moved over to the first column; while the first batch is being cleared off arginine (and lysine), the second batch is on the patient; and then the second batch is placed on the second column, the first batch is returned to the patient, the first column is being regenerated. This type of operation is in experimental clinical use for normal hemodialysis; purification is done by a non specific absorption on a conventional charcoal filter.

Animal experiments on healthy dogs

Five large (30 to 35 kg) experimental dogs were treated using extracorporeal removal of amino acids by hemodialysis. Prior to these five, three other dogs were treated using enzymatic decomposition in the extracorporeal circuit. Those findings are not directly relevant to the subject of this invention and will not be discussed here.

In the first two dogs systematic concentration of arginine could not be lowered below what appeared to be a very stiff homeostatic limit of about 100 micro moles per liter. Arginine is normally present in dog plasma at about 170 micro moles per liter (baseline, i.e. between the meals). With the blood flow of up to 0.5 liters per minute and up to 90% filter efficiency (90% reduction of the plasma arginine concentration was achieved by a single pass of the blood through three fiber filters connected in series, each with a total membrane surface of 1.8 square meters), the level of arginine was still maintained at about 100 micro molar.

Attempts to remove histidine and phenylalanine resulted in basically the same outcome—homeostatic mechanisms of controlling circulating levels of essential amino acids could not be overpowered.

While the details of this mechanism are not well understood, it is known that most of the amino acids are released by an activated breakdown of dispensable muscle proteins. Elevation of the systemic concentration of 3-methyl-histidine, which is a specific constituent of muscle proteins, points to the origin of at least some of the amino acids.

In the last three sessions on the second dog (with 12, 12 and 24 hours of deprivation) we could lower the concentration of tryptophan, which is the least frequent of the essential amino acids in the average muscular protein. The lowest value reached was about 5 micromoles/liter for free tryptophan with additional 20 micromole/liter bound to albumin. Unfortunately, deprivation of tryptophan is not as efficient in killing cancer cells as is deprivation of arginine (as shown by our in vitro work).

We have thus devised an approach combining our technique of extracorporeal blood treatment for removal of arginine (or any number of selected amino acids) with a pharmacological intervention employing an insulin/glucose clamp. As mentioned earlier, insulin is both an inhibitor of muscle protein breakdown (of both lysosomal and proteasomal pathways) and a promoter of protein synthesis. Since the net release of amino acids depends on both of these cellular activities, insulin is an excellent choice.

Figure 4:
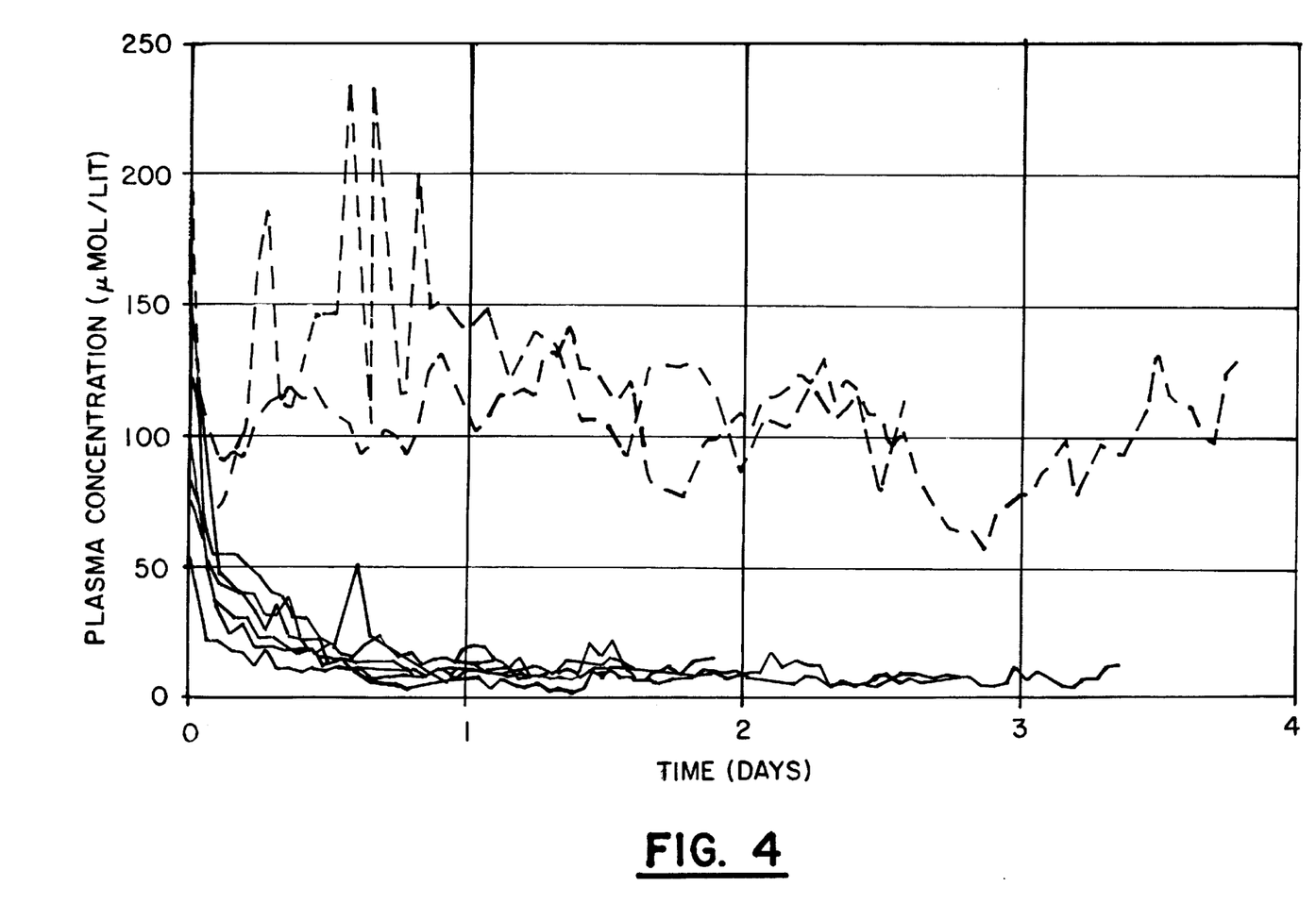
FIG. 4 shows the concentration of arginine in two dialysis sessions on experimental dogs without the use of insulin and six sessions with employment of the insulin/glucose clamp.

Six sessions on three experimental dogs lasting up to three and a half days resulted in consistent responses summarized in FIG. 4. The upper two curves (dashed lines) are from the two sessions without insulin. Not shown are the concentrations of other amino acids, which could be maintained close to their pre-set levels (determined by their concentrations in the dialyzing fluid).

A detailed description of the experiment performed on one (the first) of the last three dogs is as follows. A 30 kg dog (Anglo-Francais) 20 months old was taken into operating room under standard sterility conditions and catheters for central venous access were inserted under full anesthesia. A 50 cm long 15Fr catheter was placed through the right jugular vein into the right heart atrium (insertion length of 26 cm) and a 23 cm long 16 Fr. catheter was inserted into the left jugular vein (insertion of 15 cm), With this arrangement extracorporeal blood flow of 600 ml/min could be maintained without any problems in the fully conscious dog. Flows utilized during the experiment were typically 350 to 400 ml/min. Blood lines were passed through a corrugated plastic tube about 1.5 m long fixed on one end to a stiff collar around the neck of the dog. The other end of the corrugated tube was fed through a ball bearing attached to the cage. From there another set of 1.5 m long bloodlines were used to connect the animal to a standard dialysis machine (Fresenius 4008E). One technical modification involved lowering of the blood pump to near the floor level in order to avoid exceeding maximal suction pressures. The dog was free to move within the cage and the blood lines could be occasionally disconnected (after stopping the pump) and untwisted outside the cage. As the animal got used to the environment, we could also let him out of the cage or keep him in the cage with the doors open. At all times there was at least one person present in the room monitoring the circuits, collecting blood samples for analysis and making the needed adjustments. Blood was pumped 24 hours per day by a peristaltic pump through the filter (Fresenius F80, polysulfone, 1.8 m$^2$, 8000 Daltons cutoff, alternatively Fresenius HF80, "high flux", polysulfone, 1.8 m$^2$, 35 000 Daltons cutoff). With the dialysate flow of 350 ml/min single pass removal of arginine was 80% at the start and could be maintained at about 60 to 70% for up to 36 hours.

Concentrations of amino acids in the blood plasma were measured on an amino acid analyzer (Pharmacia, Biochrom 20) using standard procedures of sample preparation. Using a short column and a truncated buffer program, several amino acids (phenylalanine, histidine, 3-methyl-histidine, tryptophan, lysine, and arginine) could be measured in about 30 minutes of analyzer running time. Blood was sampled at the entry to the filter every hour and at the exit from the filter every second hour.

Dialysate concentrate was prepared using a standard formulation from Fresenius (HDK-F 02) as a base and adding amino acids, water-soluble vitamins; potassium chloride and sodium chloride (in addition to those of the standard formulation) and antibiotics according to Table 1. Protocol for preparation of the dialysate concentrate solutions is given in Appendix A. All substances were purchased form either Sigma or Fulka general chemical suppliers.

Two infusion pumps were used to deliver insulin and glucose to the blood into the so called bubble catcher compartment of the return bloodline. 160 units of insulin (ACTRAPID HM, Novo Nordisk) were diluted in the 100 ml of normal saline. Glucose solution was prepared fresh with 500 g of glucose per 1 liter of solution, balanced with HCl to pH 7.35). Phosphate can not be added to the concentrate (containing calcium chloride) because it would cause precipitation of calcium phosphate. Yet normal concentration of phosphate is considered important for maintenance of thrombocytes.

Standard heparin (LIQUEMIN, Roche) was delivered by the syringe pump of the dialysis machine. Fifteen minutes before the start 1000 units were injected through the catheter as bolus, and 2000 units were injected into the saline-filled extracorporeal circuit. For the continuous delivery by the syringe pump, xxx units were diluted in 24 ml of normal saline. Activated clotting time (ACT) of the blood was monitored at hourly intervals by a HEMOCHRON monitor and heparin infusion rates (usually between 0.5 and 1 ml/hr) were adjusted to keep the ACT at around 180 seconds.

We started the experiment without infusion of insulin, and as before, could not lower the level of arginine (one of the upper two curves on FIG. 4). Adding insulin to the dialysate was found to give unpredictable transport across the membrane (which quickly gets coated by blood proteins and may change its effective cut-oft). We have thus opted for direct infusion of insulin and glucose, which readily allowed for a reduction of arginine level to as little as 1.5 micromolar. This was accomplished with moderate blood flows of 300 to 400 ml/min and a single filter, of either normal, or of high flux type. Dialysate flow was normally set to 500 ml/min; occasionally, for technical reasons, to 350 ml/min.

Typical infusion rates were 100 ml/hour for glucose (delivering 50 grams of glucose per hour) and 5 to 10 ml/hour for insulin (delivering 8 to 16 units of insulin per hour). We have at times reached peak infusion rates of 140 ml/hr of glucose and 30 ml/hr of insulin solution. Blood level of glucose was monitored in hourly intervals and was maintained between 4 and 6 mmol/l (normal for dogs).

Sodium phosphate solution was infused at the rate of 30 ml/hr (delivering 1.5 grams of sodium phosphate per hour). This maintained the normal blood levels of phosphate. The amount of sodium chloride in the normal concentrate for dialysis was found to be marginal for dogs and we have subsequently increased it by adding 300 grams of NaCl to 10.5 liters of the concentrate. With this modification and by slight adjustments allowed by the mixing ratio of the concentrate and the water, we could maintain concentrations of all major salts within the normal range for dogs. Ultrafiltration rate on the dialysis machine was adjusted to result in the net rate of fluid infusion of about 75 ml/hr. The temperature of the dialysate was set to 35 deg C.; rectal temperature of the dog was in the normal range with about 38 deg C. on average.

FIG. 4 shows six sessions (solid curves) performed on three dogs using this basic protocol. No systemic problems were seen that would indicate serious threats caused by the lack of arginine. As discussed earlier, loss of thrombocytes was the main factor limiting duration of the sessions. In the last two sessions on the last dog we used yet another infusion pump to deliver iloprost (ILOMEDIN), Schering), a stable analog of prostacyclin (at 0.5 to 1.0 ng/kg/hr). The dose was perhaps too low, and we have achieved a slight prolongation only. By deployment of the approaches described earlier (oxygen supply) this problem will certainly be resolved.

In the last experiment we have identified another source of arginine which can be eliminated if further reduction proves necessary. Intestinal bacteria can produce significant amounts of amino acids, and we have measured the concentration of arginine in feces from the colon of 600 to 800 micromolar. This can be resolved by giving appropriate antibiotics orally (e.g. vancomycin) several days before the treatment and by, of course, limiting the dietary take of protein (which we did).

All five dogs survived the treatments, recovered quickly, and were placed with private owners.

Preparation of the Concentrate Solutions

A standard concentrate (35 times) from Fresenius, HDK-F 02, was used as a basis. Total contents of a 10 liter container are:

| | |
|---|---|
| Sodium chloride | 2148.0 g |
| Potassium chloride | 52.2 g |
| Calcium chloride 2 H$_2$O | 90.0 g |
| Magnesium chloride 6 H$_2$O | 71.2 g |
| Sodium acetate 3 H$_2$O | 1667.0 g |

To this we added 300 g of sodium chloride and 98 g if Potassium chloride. This is close to the limits of solubility;

magnetic stirrer was used to dissolve all additives in the original container (closed and placed on its side) during approx. 2 hours. Amino acids which are readily dissolved in water were dissolved directly in the container. Others (leucine, isoleucine methionine, cystine, phenylalanine and tyrosine) were dissolved in 200 ml of 6% HCl; this solution was added to the container and mixed in. The mixture was then slowly brought to approx. pH 7 using 5 NaOH. Water soluble vitamins (choline chloride, myo-inositol, niacinamide, d-pantothenic, pyridoxal, riboflavin, thianine) were then added to the container and dissolved. Folic acid and d-biotin were dissolved in 25 ml of 1N NaOH and added to the container. Antibiotics (4 ml of 10% BAYTRIL and 8.5 g of CLAMOXYL) were dissolved in 170 ml of normal saline and added to the mixture. Finally pH of the concentrate was adjusted to 7.5 using 5N NaOH (diluted with 34 parts of water, the final dialysate pH was 7.4). Table 1 lists all of the additives and the amounts used in our last two sessions (on the last dog). Certain adjustments were done in the course of the in vivo experiment. Note the absence of arginine, lysine, citrulline and ornithine. The goal was the removal of arginine; for reasons mentioned in the disclosure, we omitted these other three amino acids. Glutamic acid (glutamate) was added at a higher concentration than normally found in dog plasma (for it is reported inhibitory effects on protein breakdown). Taurine and glutamine were added at concentrations which are at the maximum of the normal reported range. These acids are considered important for the maintenance of the normal function of the central nervous system (specifically for the control of the osmotic pressure and for the production of neurotransmitters).

We claim:

1. A method for the treatment of tumors in a patient comprising systemic removal of an essential amino acid from the blood by extracorporeal treatment of the patient's blood comprising the steps of:
   removing blood from the patient;
   treating the blood to remove at least one essential amino acid by molecular exchange between the blood and a dialyzing fluid;
   returning the blood to the patient, wherein concurrent with said treatment of the blood, the patient is administered an effective amount of a composition which limits the release of muscular protein amino acids.

2. The method of claim 1 wherein the dialyzing fluid contains all of the essential amino acids except those to be removed from the patient's blood.

3. The method of claim 1 further comprising the step of adding all of the essential amino acids except those to be removed from the patient's blood to the treated blood before it is returned to the patient.

4. A method for the treatment of tumors in a patient comprising systemic removal of at least one essential amino acid from the blood by extracorporeal treatment of the patient's blood by molecular exchange between the blood and a dialyzing fluid which contains most of the essential low-molecular substances found in blood plasma with the exception of at least one of the essential amino acids to be removed, wherein concurrent with said treatment of the blood, the patient is administered an effective amount of a composition which limits the release of muscular protein amino acids.

5. The method of claim 4 wherein the essential amino acid to be removed is arginine.

6. The method of claim 4 wherein the patient is treated for about two to about nine days and the amino acid to be removed is arginine.

7. The method of claim 6 wherein the blood levels of arginine are lowered to, and maintained at, 10 micromoles per liter or lower during the treatment.

8. The method of claim 4 wherein the release of muscular protein amino acids is limited by a pharmacological intervention deploying an insulin/glucose clamp.

9. The method of claim 8 wherein the release of muscular protein amino acids is further limited by lowering the patient's blood temperature and blood volume.

10. The method of claim 1 further comprising treatment with chemotherapy.

11. A method for the treatment of tumors in a patient comprising the steps of:
    1) systemically removing an essential amino acid by extracorporeal treatment of the patient's blood by molecular exchange between the blood and a dialyzing fluid;
    2) adding by infusion all of the essential low molecular substances found in blood plasma with the exception of the amino acid to be removed;
    3) concurrent with said removal of the essential amino acid, administering to the patient an effective amount of a composition which limits the release of muscular protein amino acids.

12. The method of claim 11 wherein the essential amino acid to be removed is arginine.

13. The method of claim 1 further comprising the step of delivering an arginine degrading enzyme to the lungs of the patient.

* * * * *